(12) United States Patent
Jain et al.

(10) Patent No.: US 9,402,808 B2
(45) Date of Patent: Aug. 2, 2016

(54) LIQUID ORAL COMPOSITION OF LANTHANUM SALTS

(75) Inventors: Rajesh Jain, New Delhi (IN); Sarabjit Singh, New Delhi (IN); Paramjit Singh, New Delhi (IN); Pirthi Pal Singh, New Delhi (IN)

(73) Assignee: PANACEA BIOTEC LIMITED, New Delhi (IN)

( * ) Notice: Subject to any disclaimer, the term of this patent is extended or adjusted under 35 U.S.C. 154(b) by 0 days.

(21) Appl. No.: 13/979,997

(22) PCT Filed: Jan. 17, 2012

(86) PCT No.: PCT/IN2012/000041
§ 371 (c)(1),
(2), (4) Date: Jul. 16, 2013

(87) PCT Pub. No.: WO2012/098562
PCT Pub. Date: Jul. 26, 2012

(65) Prior Publication Data
US 2013/0302383 A1  Nov. 14, 2013

(30) Foreign Application Priority Data

Jan. 19, 2011  (IN) .............................. 125/DEL/2011

(51) Int. Cl.
| | | |
|---|---|---|
| *A61K 33/24* | (2006.01) | |
| *A61K 47/02* | (2006.01) | |
| *A61K 9/00* | (2006.01) | |
| *A61K 47/14* | (2006.01) | |
| *A61K 47/26* | (2006.01) | |
| *A61K 47/38* | (2006.01) | |

(52) U.S. Cl.
CPC .............. *A61K 9/0053* (2013.01); *A61K 9/0095* (2013.01); *A61K 33/24* (2013.01); *A61K 47/02* (2013.01); *A61K 47/14* (2013.01); *A61K 47/26* (2013.01); *A61K 47/38* (2013.01)

(58) Field of Classification Search
CPC ....... A61K 33/24; A61K 47/02; A61K 47/14; A61K 47/26; A61K 47/38; A61K 9/0053; A61K 9/0095
See application file for complete search history.

(56) References Cited

U.S. PATENT DOCUMENTS 7,381,428 B2 * 6/2008 Ferdinando et al. .......... 424/715
2007/0141161 A1 * 6/2007 Shaw et al. ................... 424/489

FOREIGN PATENT DOCUMENTS

JP          2007-291197 A      11/2007

OTHER PUBLICATIONS

Damment et al. "Systemic lanthanum is excreted in the bile of rats", Toxicology Letters; 171; 69-77; Apr. 24, 2007.*
"Contrast Agent for Radiography", Disclosed by George William Luckey, Research Disclosure, Mason Publications, Nov. 1, 1978, vol. 175, No. 78.*
Behets Geert J. Et al. "Localization of Lanthanum in Bone of Chronic Renal Failure Rats after Oral Dosing with Lanthanum Carbonate", Kidney International, May 2005, p. 1830-1836, vol. 67, No. 5.*
Anonymous, Disclosed by George William Luckey, "Contrast Agent for Radiography," Research Disclosure, Mason Publications, Nov. 1, 1978, vol. 175, No. 78, Hampshire, GB.
Behets Geert J. et al., "Localization of Lanthanum in Bone of Chronic Renal Failure Rats After Oral Dosing With Lanthanum Carbonate." Kidney International, May 2005, pp. 1830-1836, vol. 67, No. 5.
International Search Report for International Application No. PCT/IN2012/000041 dated Sep. 21, 2012.

* cited by examiner

*Primary Examiner* — Audrea Buckley
(74) *Attorney, Agent, or Firm* — Fanelli Haag PLLC; Parithosh K. Tungaturthi

(57) ABSTRACT

The present invention relates to liquid oral pharmaceutical compositions of lanthanum and its pharmaceutically acceptable salts thereof. The present invention further relates to preparation of liquid oral pharmaceutical compositions of lanthanum and its salts and also provides use of such compositions in treating hyperphosphatemia in patients.

11 Claims, 1 Drawing Sheet

LIQUID ORAL COMPOSITION OF LANTHANUM SALTS

FIELD OF THE INVENTION

The present invention relates to a pharmaceutical liquid oral composition of lanthanum and its pharmaceutically acceptable salts thereof. The present invention also relates to preparation of a pharmaceutical liquid oral formulation of lanthanum carbonate and also provides use of such compositions in treating patients in need thereof.

BACKGROUND OF THE INVENTION

Inorganic phosphorous is essential for multiple biological functions such as intracellular signal transduction, production and function of cell membranes and energy exchange. Although more than 80% of total body phosphorous is stored in bones and teeth phosphorous is also found in the serum, primarily as phosphate anions such as $H_2PO_4^-$ and $H_2PO_4^{2-}$.

Normal kidneys filter large amounts of organic phosphate of which more than 90% is reabsorbed by the renal tubules. Early renal dysfunction reduces filtered phosphate but also decreases tubular reabsorption, so that the urinary phosphate excretion continues to match gastrointestinal (GI) absorption. Consequently, the net balance between phosphate input and output is maintained for a period of time with only little change in serum phosphate levels. However, in patients with chronic kidney disease (CKD) Stage IV or stage V (also known as end stage renal disease ESRD), this homeostatic mechanism fails resulting in positive phosphate balance and progressive hyperphosphatemia. Hyperphosphatemia is a condition where the serum phosphate levels are greater than 5 mg/dL in adults or 7 mg/dL in children or adolescents.

Secondary hyperparathyroidism, renal osteodystrophy and soft tissue calcification are important consequences of hyperphosphatemia. Inadequate control of serum phosphorus contributes to elevated calcium-phosphorus product (CaxP) which can lead to calcification of the cardiovascular system, including the myocardium, cardiac valves, and coronary arteries. This calcification is the major cause of death in end-stage renal disease (ESRD)

Consequently, phosphate control remains an important therapeutic target in management of CKD, not only to halt progression to secondary hyperparathyroidism but also to reduce the risk of vascular calcification and cardiovascular mortality. Treatment of hyperphosphatemia includes reduction in dietary intake of phosphate; removal of phosphate with dialysis and inhibition of intestinal phosphate absorption with phosphate binders.

A typical diet includes 1000-1200 mg of dietary phosphate per day from foods such as diary products, meats whole grains of which 800 mg is ultimately absorbed. Dietary phosphate reduction can help control serum phosphate levels but because most dietary phosphate is derived from protein, it is difficult to achieve phosphate control without significant reductions in protein intake. Low-phosphate diets are unpalatable and the risk of protein malnutrition outweighs any benefit of controlling serum phosphate levels.

Kinetic studies of hemodialysis have shown that since phosphate is predominantly intracellular, serum levels drop rapidly in the first 1-2 hours of dialysis and then reach a plateau. They then rise relatively quickly in the first few hours after termination of dialysis, the so-called 'rebound phenomenon.' The administration of dietary phosphate binders is therefore necessary in most patients on dialysis to effectively manage their hyperphosphatemia.

Phosphate binders are more effective at binding dietary phosphate than endogenous phosphate. Therefore, phosphate binders are currently administered with meals, to bind dietary phosphate before it is absorbed by the body and thus optimize the phosphate binding efficiency.

Use of aluminum-based phosphate binders was largely abandoned because of concerns over accumulation and major toxicities including dialysis encephalopathy, cognitive disturbances and osteomalacia. Calcium-based agents replaced aluminum but their prolonged administration can result in hypercalcemia. In addition they can result in over-suppression of parathyroid hormone (PTH), and can cause both soft tissue and vascular calcification. Magnesium-containing phosphate binders can be used as an alternative to calcium-based agents but generally they are less effective, and are associated with increased serum magnesium levels and diarrhea. Sevelamer hydrochloride was the first synthetic non-aluminium and calcium-free phosphate binder to become available. Metabolic acidosis, and cost are limiting factors affecting the wider use of sevelamer hydrochloride.

The need for effective treatments with better safety profiles led to the introduction lanthanum carbonate. Lanthanum carbonate is a known phosphate binder and is used to reduce phosphate levels in patients with hyperphosphatemia specifically those patients with hyperphosphatemia caused by end stage renal disease. Lanthanum carbonate is currently available from Shire US Inc. in 500, 750, and 1000 mg chewable tablets, marketed under the trade name, Fosrenol®.

U.S. Pat. No. 5,968,976 describes the use of $La_2(CO_3)_3 \cdot xH2O$, where x has a value of 3 to 6, for the preparation of a medicament for the treatment of hyperphosphataemia by administration into the gastrointestinal tract. The patent discloses dosage forms for oral administration like solid forms such as tablets, capsules and suspensions or syrups. Though this patent discloses word "suspension" as a dosage form, suspensions have not been exemplified or taught anywhere in the specification United States Patent Application 2008/0125394 relates to a continuous slow release oral pharmaceutical compositions of substances capable of binding phosphorus, which when administered during fasting periods provides an improved treatment of hyperphosphatemia by binding the phosphorous secreted in the saliva and other gastric secretions. This patent explicitly describes about determination of phosphorus in saliva, binding the phosphorus that are secreted in saliva. And thus the compositions need to be retained in mouth for long period of time; the formulations include chewing gums, chewable tablets, powders, etc.

PCT application WO2004/016553 relates to rare earth metal compounds of porous nature. The patent application further relates to the method of making the rare earth metal compounds and methods of using said rare earth metal compounds. The patent application specifically relates to the lanthanum oxychloride, anhydrous lanthanum oxycarbonate, and hydrated lanthanum oxycarbonate having porous structure and improved phosphate binding capacity.

Despite the merits of the above mentioned compositions, the management of hyperphosphatemia in patients with chronic kidney disease remains challenging.

Chewable tablets are the only dosage form available for patients currently. The current dosage form carries many drawbacks for the treatment of hyperphosphatemia. Although chronic kidney disease (CKD) is found in persons of all ages, the highest incidence rate of end stage renal disease (ESRD) occurs in patients older than 65 years. As per the National Health and Nutrition Examination Survey (NHANES) III data, the prevalence of chronic kidney disease was 37.8% among patients older than 70 years. Patients older than 60 years of age have difficulties in chewing. The surface area of the lanthanum carbonate depends upon the thoroughness of the patient's chewing, resulting in a wide variance of effectiveness of phosphate binding.

Additionally for patients who have dentures, who are intubated and who are receiving enteral tube feedings who are unable to chew; medications are commonly crushed and administered through the nasogastric tube. Since lanthanum powder is un-dissolvable in liquids these tablets when crushed, remain as large granules, even after a period of many hours. This significantly reduces phosphate binding efficacy.

Furthermore, Fosrenol® chewable tablets are of substantial size, ranging in diameter from 18 mm for the 500 mg strength and 22 mm for the 1000 mg strength. The US Food and Drug Administration (FDA) has recently added lanthanum carbonate to the list of drugs to be monitored based on potential signs of serious risks specifically to monitor any swallowing complications, gastrointestinal obstruction (attributed to tablet hardness).

Also, Phosphate binders like lanthanum carbonate are only one of the many medications that patients with stage 5 chronic kidney disease are prescribed. A recent survey, suggests that patients undergoing dialysis treatment were prescribed an average of 12 different medications. The cumulative effect of multiple dosing regimens can impose a confusing and possibly overwhelming burden on a patient. In addition this high daily tablet burden associated with phosphate binders may contribute to poor patient adherence.

Furthermore patients suffering from End Stage Renal Disease (ESRD), severely injured patients, elderly or senile patients, mentally handicapped patients or other patients may require special administration of the Lanthanum carbonate. Liquid formulations, for example solutions, suspensions, dispersion etc, provide ease of administration and increase compliance among certain patient populations by enhancing taste and/or texture of the drug being administered.

At the moment, Lanthanum salts/compounds are not available as a liquid formulation at all but only as a solid tablet. As elucidated above the considerable size of chewable tablets coupled with poor patient compliance leads to inadequate therapeutic delivery. Thus there exists an unmet need in the current armamentarium of physician to treat chronic kidney disease.

OBJECTS OF THE INVENTION

A need remains for developing new liquid pharmaceutical dosage forms of lanthanum carbonate for administration to the compromised patient. Therefore, the present invention relates to oral liquid formulations of lanthanum carbonate which includes monophasic and biphasic formulations such as solutions, syrups, suspension, dispersion, emulsion.

It is an object of the present invention to provide a liquid oral pharmaceutical composition comprising therapeutically effective amount of lanthanum and its pharmaceutically acceptable salts thereof and at least one suspending agent that is sufficient to form a stable, easily re-suspendable suspension of said lanthanum.

In another aspect the present invention relates to liquid oral formulations of lanthanum and its pharmaceutically acceptable salts thereof, suspended using a suspending agent in a suspending/carrier medium or vehicle which is aqueous or non-aqueous in nature.

In another object, the present invention relates to liquid oral formulations of lanthanum and its pharmaceutically acceptable salts thereof, wherein the liquid oral formulation comprises from 0.1% to about 50% of elemental lanthanum by total weight of the composition.

In further object, the present invention relates to liquid oral formulations of lanthanum and its pharmaceutically acceptable salts thereof, wherein the liquid oral formulation comprises 5-500 mg/ml of lanthanum carbonate.

In further object, the present invention relates to liquid oral formulations of lanthanum and its pharmaceutically acceptable salts thereof, wherein the suspension comprises of 25-350 mg/ml of lanthanum carbonate.

In another object, the present invention relates to liquid oral formulations of lanthanum and its pharmaceutically acceptable salts thereof, wherein the suspension comprises 0.1-25% lanthanum and 75-99.9% excipients and suspending medium.

Yet another object of the present invention relates to liquid oral formulations of lanthanum and its pharmaceutically acceptable salts thereof, wherein the suspension is used for the treatment of hyperphosphatemia.

In another object the present invention relates to pharmaceutical suspensions of lanthanum and its pharmaceutically acceptable salts thereof wherein 90% of the suspended particles have a particle size diameter of less than 300µ; 50% of the particles have a particle size diameter of less than 200µ and 10% of the particles have a particle size diameter of less than 150µ.

Yet another object of the present invention relates to liquid oral formulations of lanthanum and its pharmaceutically acceptable salts thereof, wherein the suspension exhibits an invitro release of at least 75% in 15 minutes.

Yet another object of the present invention relates to liquid oral formulations of lanthanum and its pharmaceutically acceptable salts thereof, wherein the suspension exhibits an in-vitro release of 95% in 15 minutes.

Yet another object of the present invention relates to liquid oral formulations of lanthanum and its pharmaceutically acceptable salts thereof, wherein the suspension exhibits a sedimentation ratio between 0.5 to 1.

In another object, the present invention relates to liquid oral formulations of lanthanum and its pharmaceutically acceptable salts thereof wherein the particles remain homogenously dispersed upon shaking for at least 1 day to about 2 years.

In another object, the present invention relates to liquid oral formulations of lanthanum and its pharmaceutically acceptable salts thereof wherein the composition is present in the form of dry powder for reconstitution.

DETAILED DESCRIPTION OF THE INVENTION

Figure 1:
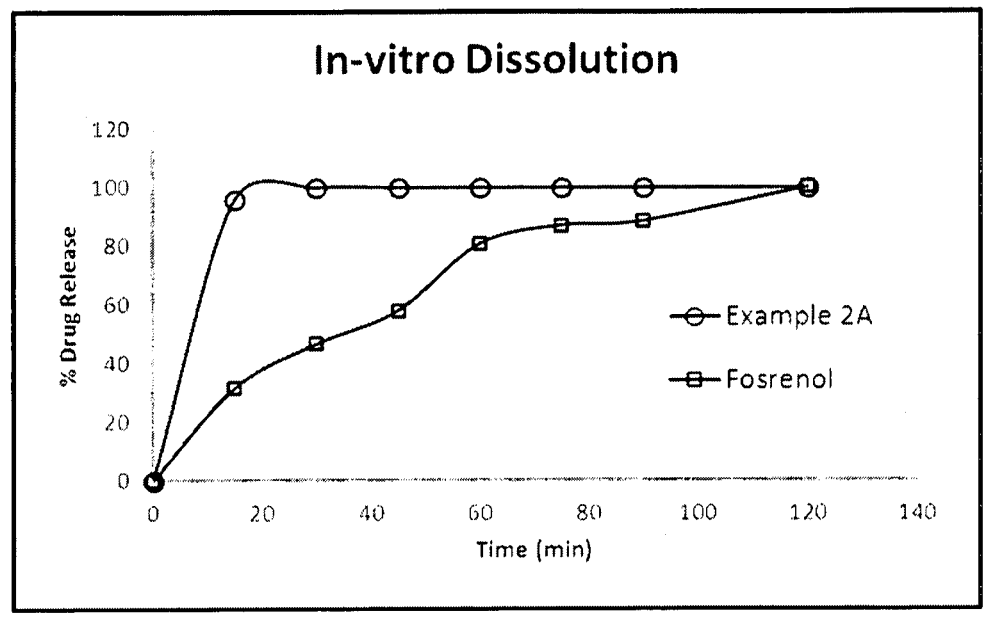
FIG. 1 illustrates dissolution of suspension prepared in Example 2A vs. Forsenol® chewable tablet in 1000 ml 0.25N HCL using USP Type-II dissolution apparatus at 50 rpm
Figure 2:
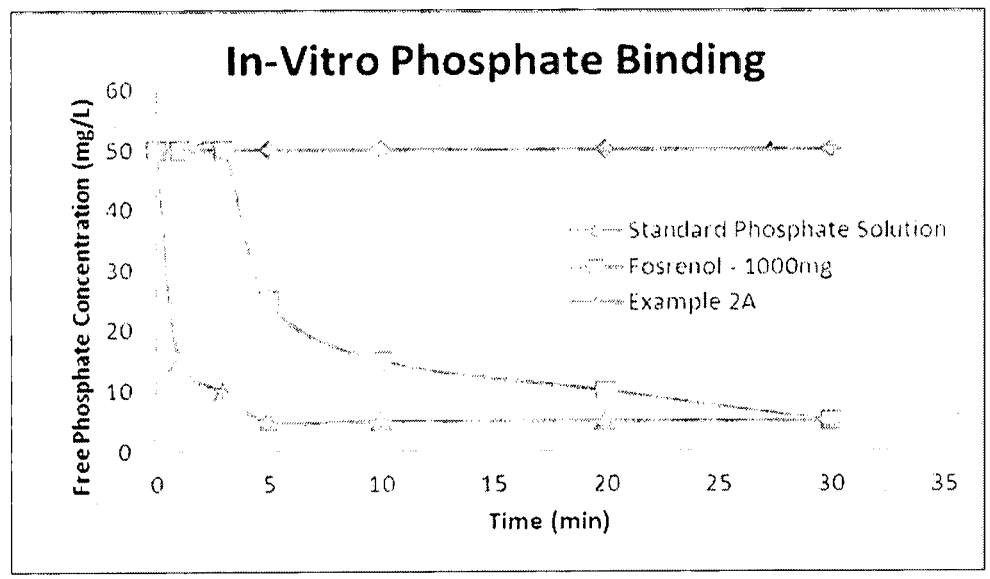
FIG. 2 illustrates rate of phosphate binding of suspension prepared in example 2A vs. Forsenol® chewable tablets of strength 1000 mg

"Lanthanum and its pharmaceutically acceptable salts" according to the present invention includes all the salts of lanthanum metal for example, lanthanum carbonate lanthanum hydroxy carbonate, lanthanum oxy carbonate, lanthanum oxide, lanthanum acetate, lanthanum chloride, lanthanum bromate, lanthanum iodate, lanthanum molybdate, lanthanum nitrate, lanthanum selenate, lanthanum sulfate, lanthanum tungstate's, lanthanum chromate or the like or combinations thereof.

Liquid oral formulation of the present invention may be prepared using any of the known excipients and processes known in the prior art, the contents of which are incorporated herein by reference in their entirety.

The pharmaceutical composition of the present invention is described as a suspension. A suspension is one in which solid particles of one or more active substances are suspended within a suspending or carrier medium. The suspending or carrier medium may be aqueous or non-aqueous in nature. The suspending medium or carrier medium may contain various excipients for example but not limited to suspending or thickening agents, flavouring agents, sweetening agents coloring agents and buffering agent.

The composition of the present invention is also described as being stable. A stable suspension is one which can be re-dispersed or re-suspended with light to moderate shaking throughout its shelf life thereby resisting caking or sedimentation. In addition a stable suspension is one in which the suspended active agent is not substantially degraded nor is its release substantially affected over the course of its shelf life. It is desirable that the suspension is stable for a period of at least 6 months preferably 1 year more preferably 2 years. Storage stability is typically measured with respect to ambient relative humidity which ranges from 50% to 85% and temperature which usually ranges from 25° C. to 60° C.

"About" will be understood by persons of ordinary skill in the art and will vary to some extent on the context in which the term is used. If there are uses of the term which are not clear to persons of ordinary skill in the art given the context in which it is used, "about" will mean up to plus or minus 10% of the particular term.

Lanthanum is a naturally occurring rare-earth element with a molecular weight of 138.9 Da and atomic number 57. As a phosphate binder, lanthanum is ingested as the carbonate salt, and it dissociates in the upper GI tract to form lanthanum ions ($La^{3+}$). Lanthanum ions bind phosphate ionically, optimally at pH 3-5, while retaining its phosphate-binding capacity across the full pH range from 1 to 7. The chemical basis for this ionic binding is the properties of $La^{3+}$ which has an overwhelming preference for oxygen donor atoms of which the most common ligands are $PO_4$ groups. Lanthanum forms insoluble complexes with phosphate that are eliminated via feces.

Tablets have to undergo disintegration before dissolution which is the rate limiting factor in phosphate binding. The size or diameter of suspended lanthanum salt determines the rate and extent of ionization and consequently the rate of phosphate binding. The surface area of lanthanum carbonate chewable tablets is dependent on thoroughness of patients chewing. As elucidated in the foregoing discussion the tablets have high hardness which leads to inadequate chewing and consequently variable particle size. Large particle size exposes less surface area, thus leading to incomplete or delayed ionization of lanthanum ions. This results in wide variance in rate of phosphate binding.

In contrast, applicants have surprisingly found that the pharmaceutical suspensions of lanthanum according to the present invention by virtue of the formulation characteristics of being in liquid form and with specific particle size, exposes more surface area thus leading to rapid and complete ionization in the gastrointestinal tract to form lanthanum ions which bind to dietary phosphate at a significantly faster rate than other commercially available dosage forms. This is evidenced by the increase in rate of phosphate binding as exemplified in Example 11; Table 6.

The preferred lanthanum salt used in the suspensions according to the present invention is lanthanum carbonate. Anhydrous lanthanum carbonate or lanthanum carbonate hydrates can be used.

In another embodiment, the liquid oral compositions according to the present invention comprises from about 0.1% to about 50% of elemental lanthanum by total weight of the composition. In a preferred embodiment the amount of elemental lanthanum is from about 0.1% to about 25% by total weight of the composition.

In another embodiment the suspension comprises 5-500 mg/ml of lanthanum carbonate. In a preferred embodiment the suspension comprises 25-150 mg/ml of lanthanum carbonate.

The pharmaceutical compositions in accordance with the present invention are preferably prepared by suspending lanthanum carbonate in a suspending medium by using a suspending agent. Non-limiting examples of suspending agent or thickening agent for pharmaceutical products that can be included in the suspension of the present invention include, oligosaccharides, polysaccharides such as xanthan, guar and tragacanth gums, cellulose derivatives HPMC (hydroxypropyl methylcellulose), microcrystalline cellulose (marketed under the trade name Avicel® by FMC Biopolymer Corp.), microcrystalline cellulose/sodium carboxymethyl cellulose (marketed under the trade name Avicel® RC 591 by FMC Biopolymer Corp.), Carbopol, carboxyvinyl polymer, Polyvinylpyrrolidone (PVP), acacia, povidone, alginic acid, sodium alginate, propylene glycol, alginate, carbomer, carboxymethylcellulose calcium, ethylcellulose, gelatin, hydroxyethyl cellulose, hydroxypropyl cellulose, polydextrose, carrageenan, methylcellulose, sucrose, sorbitol, xylitol, dextrose, fructose, malitol, sugar, sodium alginate, bentonite, a polyvinyl alcohol, cetearyl alcohol, colloidal silicon dioxide and mixtures thereof.

Optionally suspending agents may be in the preparation of suspensions according to the present invention. Suspending agent used in the present invention is in the concentration of 0.005-15% by total weight of the composition. A concentration of 1.5% by total weight of the composition is especially desirable.

Sweeteners may be utilized as part of the suspension to enhance organoleptic properties of the suspension and to make the dosage form more palatable to the patients. Non-limiting examples of sweeteners include sucralose, acesulfam potassium, sodium saccharin, aspartame, mono ammonium glycyrrhizinate, sorbitol 70% solution, maltitol syrup, sucrose, fructose, maltitol, crystalline or the like or combinations thereof. The sweeteners except aspartame can also function as viscosity increasing agents. The amount of sweetener used in accordance with the present invention may vary from 0.005 to 10%.

Flavoring agents and flavor enhancers may also be used to enhance the organoleptic properties of the final composition preferably in synergistic effect with the sweeteners. Common flavoring agents and flavor enhancers for pharmaceutical products that can be included in the composition of the present invention include natural, semi-synthetic or synthetic flavors, for example but not limited to, maltol, vanillin, ethyl vanillin, menthol, citric acid, fumaric acid, ethyl maltol and tartaric acid and the like or combinations thereof. Flavourants may be typically added in an amount from 0.05 to 10% with 0.01% to about 5% being especially preferable.

Optionally, pH modifiers or buffers may be used to maintain pH of the final composition within the final desired range. pH has a substantial effect on stability, so pH modifiers enhance the stability of the formulation overall. Buffering agent as used herein, refers to an agent or a mixture of agents that can maintain the original acidity or basicity of a composition. Buffering agents include, but are not limited to, citric acid, sodium citrate, sodium phosphate, potassium citrate, and mixtures thereof.

Antimicrobial agents useful in the formulations of the invention include but are not limited to sodium benzoate, sodium methyl paraben, methyl paraben, propyl paraben, sodium propyl paraben, potassium sorbate, sodium propionate. Sodium benzoate is particularly preferrred. The antimicrobial agent should not interfere with the suspended particles and should not affect the taste or pH of the final composition. The amount of antimicrobial agent used can vary from 0.01 to 5%.

Coloring agents make the dosage form more acceptable to the patients and helps in easy identification of the preferable brand. Coloring agents include, but not limited to, all FD&C dyes and colors, red oxide, titanium oxide or combinations thereof.

The remainder of the composition according to the present invention is the suspending medium or carrier medium. Suspending or carrier medium can be aqueous or non-aqueous in nature. Preferably propylene glycol dicaprylate/dicaprate is used as a suspending medium such as that currently marketed by Gattefosse, Canada as Labrafac™ PG. Aqueous or non-aqueous carrier medium is utilized in conjunction with the foregoing excipients so as to provide about 100% of the total composition.

The amount of drug released from the dosage form as exemplified in example 2A is determined by paddle method (Apparatus USP type II) by immersing the dosage form in 1000 ml 0.25N HCl. various samples of the formulation were stored for 1 month, 2 months and 6 months and the percentage of drug released from the dosage form was determined. This indicates that the percentage of drug released from dosage form is during the stability period. In an embodiment the suspension exhibits an in-vitro release of at least 75% in 15 minutes. In a preferred embodiment the suspension exhibits an in-vitro release of 95% in 15 minutes.

The size or diameter of suspended lanthanum salt determines the rate and extent of ionization and consequently the rate of phosphate binding. Larger particles tend to expose lesser surface area of the suspended lanthanum carbonate and thus results in incomplete and reduced ionization and also inadequate phosphate binding. Smaller particles on the other hand tend to expose larger surface area which leads to rapid and complete ionization and thus effective phosphate binding. This is evidenced by significantly higher rate of phosphate binding exhibited by suspensions according to the present invention when compared to Fosrenol® crushed tablets. Tablets were crushed in mortar using a pestle until no visible coarse particles were seen. This rigorous crushing of tablets mimics complete chewing as seen in an ideal scenario. As elaborated in the foregoing discussion due to various factors the ideal scenario as stated may not be possible always. Example 11 provides a suitable non-limiting method of determining rate of phosphate binding.

In an embodiment 90% of the suspended particles have a particle size diameter of less than 300μ; 50% of the particles have a particle size diameter of less than 200μ and 10% of the particles have a particle size diameter of less than 150μ.

In another embodiment 90% of the suspended particles have a particle size diameter of less than 200μ; 50% of the particles have a particle size diameter of less than 100μ and 10% of the particles have a particle size diameter of less than 50μ. In another embodiment 90% of the suspended particles have a particle size diameter of less than 100μ; 50% of the particles have a particle size diameter of less than 50μ and 10% of the particles have a particle size diameter of less than 20μ.

In a preferred embodiment, 90% of the suspended particles have a particle size diameter of less than 55μ; 50% of the particles have a particle size diameter of less than 25μ and 10% of the particles have a particle size diameter of less than 15μ. Example 7 provides a suitable non-limiting method of determining particle size.

Stability of a suspension is solely dependent on the sedimentation rate of dispersed phase, which is dependent on the viscosity of the dispersion medium. Increase in viscosity of medium, decreases settling, so the particles achieve good dispersion system but greater increase in viscosity gives rise to problems like pourability and redispersibility of suspension.

In accordance with the present invention, viscosity of the suspension remains between 80-97 centiopoise (cps) over the entire period of 6 months. In a preferred embodiment viscosity of the suspension is between 90-97 centi-poise such that it does not hinder the re-dispersibility of the sediments and at the same time ensuring ease of pourability. Example 8 provides a suitable non-limiting method of determining viscosity.

In accordance with the present invention the sedimentation ratio of the suspension is between 0.5 to 1. In a preferred embodiment sedimentation ratio of the suspension is between 0.7 to 1. More preferably the suspensions according to present invention exhibit a sedimentation ratio of between 0.9-1. Sedimentation ratio of 1 indicates that the suspension is in flocculation equilibrium. Example 9 provides a suitable non-limiting method of determining sedimentation ratio.

Compositions according to the present invention may be prepared by any suitable procedure. The following illustrative procedure may be utilized and is preferred. The process comprises the following steps:

1. 70%-80% of the total required quantity of the suspending medium was measured and transferred into a vessel equipped with a stirring element.
2. Sweetening agent, flavoring agents and antimicrobial agents were added to the dispersion of step 1 with continuous stirring.
3. Lanthanum and its pharmaceutically acceptable salts and optionally suspending agent were added to the mixture formed in Step 2, with continuous stirring.
4. The suspension of Step 3 was homogenized using suitable equipment.
5. The remaining volume was made up with suspending medium.
6. The suspension formed in Step 5 was then filled into bottles followed by secondary or tertiary packing.

The following examples are merely illustrative of the present invention and they should not be considered as limiting the scope of the invention in any way, as these examples and other equivalents thereof will become more apparent to those versed in the art in the light of the present disclosure.

Example-1

| Ingredients | Quantity (g) |
| --- | --- |
| Lanthanum carbonate | 8.25 |
| Sucralose | 0.065 |
| Menthol | 0.035 |
| Avicel RC 591 | 1.5 |

-continued

| Ingredients | Quantity (g) |
|---|---|
| Sodium methyl paraben | 0.1 |
| Sodium benzoate | 0.1 |
| Purified water | q.s. 100 mL |

Manufacturing Process:

1. 70%-80% of the total required quantity of purified water was measured and transferred into a vessel equipped with a stirring element.
2. Avicel RC 591 was added slowly to water under stirring conditions.
3. Sucralose, Menthol, Sodium methyl paraben, and sodium benzoate were added to the above dispersion with continuous stirring.
4. The mixture was stirred for about 30 minutes.
5. Lanthanum carbonate powder was added to above mixture and the mixture was stirred for 15-30 min.
6. The above suspension was homogenized using suitable equipment like high speed homogenizer, high shear homogenizer, colloidal mill, ball mill etc. for about 15 to 60 minutes.
7. The remaining volume was made up with purified water
8. The suspension formed in Step 7 was then filled into bottles followed by secondary or tertiary packing and labelling.

Example-2

| Ingredients | A | B | C |
|---|---|---|---|
| | Quantity (% w/v) | | |
| Lanthanum carbonate | 8.25 | 8.25 | 16.5 |
| Colloidal Silicon dioxide | 0.0825 | 0.0825 | 0.165 |
| Sucralose | 0.065 | 0.05 | 0.13 |
| Menthol | 0.035 | 0.05 | 0.07 |
| Avicel RC 591 | 1.5 | 3 | |
| Sodium methyl paraben | 0.1 | 0.1 | 0.2 |
| Sodium benzoate | 0.1 | 0.1 | 0.2 |
| Purified water | q.s. 100 mL | q.s. 100 mL | q.s. 100 mL |

Manufacturing Process:

1. 70%-80% of the total required quantity of purified water was measured and transferred into a vessel equipped with a stirring element.
2. Optionally Avicel RC 591 was added slowly to water under stirring conditions.
3. Sucralose, Menthol, Sodium methyl paraben, and sodium benzoate were added to the above dispersion with continuous stirring.
4. The above mixture was stirred for about 30 minutes.
5. Lanthanum carbonate powder and optionally colloidal silicon dioxide were added to above mixture and the mixture was stirred for 15-30 min.
6. The above suspension was homogenized using suitable equipment like high speed homogenizer, high shear homogenizer, colloidal mill, ball mill etc. for about 15 to 60 minutes.
7. The remaining volume was made up with purified water
8. The suspension formed in Step 7 was then filled into bottles followed by secondary or tertiary packing and labelling.

Example-3

| Ingredients | A | B |
|---|---|---|
| | Quantity (% w/v) | |
| Lanthanum Carbonate | 8.25 | 33 |
| Sucralose | 0.2 | 0.8 |
| Menthol | 0.1 | 0.4 |
| sodium benzoate | 0.15 | 0.6 |
| Labrafac PG | qs 100 mL | qs 100 mL |

Manufacturing Process:

1. 70%-80% of the total required quantity of Labrafac PG was measured and transferred into a stainless steel vessel equipped with a stirring element.
2. Sucralose, Menthol and sodium benzoate were added to the above dispersion with continuous stirring.
3. The above mixture was stirred for about 30 minutes.
4. Lanthanum carbonate powder was added to above mixture and the mixture was stirred for 15-30 min.
5. The above suspension was homogenized using suitable equipment like high speed homogenizer, high shear homogenizer, colloidal mill, ball mill etc. for about 15 to 60 minutes.
6. The remaining volume was made up with Labrafac PG.
7. The suspension formed in Step 6 was then filled into bottles followed by secondary or tertiary packing and labelling.

Example-4

| Ingredients | Quantity (% w/v) |
|---|---|
| Lanthanum Carbonate | 8.25 |
| Colloidal silicon dioxide | 0.0825 |
| Sucralose | 0.2 |
| Menthol | 0.1 |
| sodium benzoate | 0.15 |
| Labrafac PG | qs 100 mL |

Manufacturing Process:

1. 70%-80% of the total required quantity of Labrafac PG was measured and transferred into a stainless steel vessel equipped with a stirring element.
2. Sucralose, Menthol and sodium benzoate were added to the above dispersion with continuous stirring.
3. The above mixture was stirred for about 30 minutes.
4. Lanthanum carbonate powder and optionally colloidal silicon dioxide were added to above mixture and the mixture was stirred for 15-30 min.
5. The above suspension was homogenized using suitable equipment like high speed homogenizer, high shear homogenizer, colloidal mill, ball mill etc. for about 15 to 60 minutes.
6. The remaining volume was made up with Labrafac PG.
7. The suspension formed in Step 6 was then filled into bottles followed by secondary or tertiary packing and labelling.

Example-5

| Ingredients | Quantity (% w/v) |
|---|---|
| Lanthanum Carbonate | 8.25 |
| Colloidal silicon dioxide | 0.0825 |
| Sucralose | 0.2 |
| Menthol | 0.1 |
| Avicel RC 591 | 1.5 |
| sodium benzoate | 0.15 |
| Labrafac PG | qs 100 mL |

Manufacturing Process:
1. 70%-80% of the total required quantity of Labrafac PG was measured and transferred into a stainless steel vessel equipped with a stirring element.
2. Avicel RC 591 was added slowly to Labrafac PG under stirring conditions.
3. Sucralose, Menthol and sodium benzoate were added to the above dispersion with continuous stirring.
4. The above mixture was stirred for about 30 minutes.
5. Lanthanum carbonate powder and colloidal silicon dioxide were added to above mixture and the mixture was stirred for 15-30 min.
6. The above suspension was homogenized using suitable equipment like high speed homogenizer, high shear homogenizer, colloidal mill, ball mill etc. for about 15 to 60 minutes.
7. The remaining volume was made up with Labrafac PG.
8. The suspension formed in Step 7 was then filled into bottles followed by secondary or tertiary packing and labeling.

TABLE 1

Organoleptic parameters.

| Specifications | Initial | 1 month | 2 month | 6 months |
|---|---|---|---|---|
| Appearance | White uniform suspension | White uniform suspension | White uniform suspension | White uniform suspension |
| Taste | mildly sweet flavored palatable | mildly sweet flavored palatable | mildly sweet flavored palatable | mildly sweet flavored palatable |
| Redispersibility | Easily re-suspendable | Easily re-suspendable | Easily re-suspendable | Easily re-suspendable |
| Specific gravity | 1.06 | 1.070 | 1.075 | 1.068 |
| pH | 8.32 | 8.10 | 8.07 | 7.97 |
| % Drug content | 101.96 | 100.48 | 98.95 | 99.36 |

A stability analysis of the formulation as exemplified in Example 1 was undertaken. Various samples of the formulation were stored for 1 month, 2 months and 6 months and parameters such as appearance, taste, redispersibility, specific gravity and pH were determined. The suspension sediment should be loosely packed such that after minimal shaking the sediment redisperses and reforms the original suspension. The stability studies indicate that the suspension is easily re-suspendable with minimal hand shaking and maintains a uniform specific gravity and pH over a period of time. The stability analysis also indicates that the formulation is stable without any potency loss and no significant change was observed with respect to percentage drug content.

Example 7

TABLE 2

Particle size diameter of suspension.

| Specifications | | Initial | 1 month | 2 months | 6 months |
|---|---|---|---|---|---|
| Particle size diameter of lanthanum carbonate suspension (microns) | 40° C./75% RH | 10% < 11.5 | 10% < 17.4 | 10% < 18.3 | 10% < 13.9 |
| | | 50% < 18.2 | 50% < 39.9 | 50% < 40.3 | 50% < 36.8 |
| | | 90% < 48 | 90% < 63.5 | 90% < 64.0 | 90% < 48.5 |
| | 30° C./65% RH | | 10% < 18.1 | 10% < 16.0 | 10% < 14.8 |
| | | | 50% < 40.3 | 50% < 35.9 | 50% < 39.8 |
| | | | 90% < 63.8 | 90% < 60.8 | 90% < 53.5 |
| | 25° C./60% RH | | 10% < 17.3 | 10% < 16.5 | 10% < 14.8 |
| | | | 50% < 39.4 | 50% < 36.6 | 50% < 39.1 |
| | | | 90% < 63.5 | 90% < 56.0 | 90% < 52. |
| | 60° C. | | 10% < 17.9 | 10% < 16.2 | 10% < 12.4 |
| | | | 50% < 40.3 | 50% < 37.8 | 50% < 36 |
| | | | 90% < 63.7 | 90% < 59.0 | 90% < 46.1 |

Particle size diameter of suspensions as exemplified in example 1 was measured using Horriba particle size analyzer. The suspension was transferred to the sample cell using a dropper to obtain an obscuration level of 15% to 30%. At least two readings and preferably three per sample were recorded and reported as 10%, 50% and 90% undersize and tabulated in the table 2 above. At least two sample readings should be within ten percent of each other to be acceptable. The results indicate that the mean particle size diameter of the suspension over a period of 6 months remains within 20% of the mean particle size diameter of the freshly prepared suspension.

Example 8

TABLE 3

Viscosity of the suspension

| | Specifications | Initial | 1 month | 2 months | 6 months |
|---|---|---|---|---|---|
| Viscosity (centipoise) | 40° C./75% RH | 97 | 97 | 97 | 93 |
| | 30° C./65% RH | | 96 | 94 | 92 |
| | 25° C./60% RH | | 95 | 90 | 91 |
| | 60° C. | | 86 | 84 | 80 |

Viscosity of the suspension as exemplified in example 1 was measured using Brookfield Viscometer. The viscosity of the suspension remains between 80-97 centipoise (cps) over the entire period of 6 months. The results indicate that the suspension has optimal viscosity such that it does not hinder the re-dispersibility of the sediments and at the same time ensuring ease of handling.

Example 9

TABLE 4A

Sedimentation ratio

| | Specifications | Initial | 1 month | 2 months | 6 months |
|---|---|---|---|---|---|
| Sedimentation ratio | 40° C./75% RH | 1 | 0.90 | 0.77 | 0.70 |
| | 30° C./65% RH | | 0.93 | 0.83 | 0.73 |
| | 25° C./60% RH | | 0.89 | 0.86 | 0.70 |
| | 60° C. | | 0.80 | 0.75 | 0.71 |

TABLE 4B

Sedimentation ratio

| | Specifications | Initial | 1 month | 2 months | 6 months |
|---|---|---|---|---|---|
| Sedimentation ratio | 40° C./75% RH | 1 | 0.96 | 0.94 | 0.90 |
| | 30° C./65% RH | | 0.97 | 0.96 | 0.93 |
| | 25° C./60% RH | | 0.98 | 0.96 | 0.93 |
| | 60° C. | | 0.81 | 0.82 | 0.72 |

Sedimentation means settling of particle or flocculates occur under gravitational force in liquid dosage form. Tables 4A and 4B illustrate the sedimentation ratio of suspensions as herein exemplified in example 1 and example 2A respectively. Sedimentation ratio of the suspension as exemplified in example 1 was measured. 100 ml of the suspension was transferred from the bulk after shaking in a 100 mL graduated cylinder and allowed to stand. The height occupied by the solute in the cylinder below the supernatant (clear surface of the suspension) was noted as the height of the sediment.

Sedimentation ratio is calculated using the following formula.

$$F = H_u / H_O$$

Wherein, $H_u$=final or ultimate height of sediment $H_O$=original height of suspension before settling F=1, such product is said to be in flocculation equilibrium. The results are tabulated in the table above.

Example 10

TABLE 5

In vitro dissolution

| | Specifications | Initial | 1 month | 2 months | 6 months |
|---|---|---|---|---|---|
| Dissolution (% released in 15 min) | 40° C./75% RH | 102.83 | 100.99 | 98.67 | 100.62 |
| | 30° C./65% RH | | 99.84 | 99.05 | 99.48 |
| | 25° C./60% RH | | 100.83 | 98.15 | 101.44 |
| | 60° C. | | 106.08 | 99.50 | 101.11 |

The amount of drug released from the dosage form as exemplified in example 2A was determined by paddle method (Apparatus USP type II) by immersing the dosage form in 1000 ml 0.25N HCl. Various samples of the formulation were stored for 1 month, 2 months and 6 months and the percentage of drug released from the dosage form was determined. The results are tabulated in Table 5 above.

Example 11

TABLE 6

Phosphate binding studies

| Time (min) | Standard Phosphate Solution (mg/l) | Concentration of unbound phosphate | |
|---|---|---|---|
| | | Fosrenol ® - 1000 mg (crushed) | Example 1 |
| 0 | 50 | 50 | 50 |
| 1 | 50 | 50 | 15 |
| 3 | 50 | 50 | 10 |
| 5 | 50 | 25 | 5 |
| 10 | 50 | 15 | 5 |
| 20 | 50 | 10 | 5 |
| 30 | 50 | 5 | 5 |

Phosphate binding ability is term used to predict amount of phosphate that can be bound by a sequestrant. Phosphate binding capacity of suspensions as exemplified in example 2A is compared with Forsenol® chewable tablets of strength 1000 mg. Stock solution of potassium phosphate was prepared in distilled water (10,000 mg/l of phosphate ion). The Solution thus obtained was Stock 1.10 mL of stock I was diluted to 100 mL with 0.1N HCl (1,000 mg/l) to produce Stock II. Tablets were crushed in mortar using a pestle until no visible coarse particles were seen. This rigorous crushing of tablets mimics complete chewing as seen in an ideal scenario. 28.5 mL of 0.1N HCl was added into 50 mL beaker and 1.5 mL of stock II solution was added and mixed using magnetic stirrer. At 0 time point weighed quantity of lanthanum carbonate tablet powder or lanthanum carbonate suspension was added into the beaker under stirring condition. Aliquots were removed after 1, 3, 5 10, 30 and 60 min and analysed for free phosphate ion concentration using Quantofix®. 5 mL of aliquot is added into the beaker supplied in the kit 0.5 drops of solution A, supplied in kit, was added into the beaker containing 5 mL aliquot and was vortexed for 10 sec. 6 drops of solution B, supplied in kit, was added into small 1 mL test tube that was supplied along with the kit. One strip, supplied in kit, was removed from the pack and dipped in beaker for 15 sec. The excess liquid on the strip was removed by jerking. The same strip was then inserted into the 1 ml test tube for 15 seconds and excess liquid was drained off. The color of the strip was observed and matched with the standard colors supplied in kit.

Rate of phosphate binding can be calculated by the formula $$\text{Rate of phosphate binding} = \frac{[\text{Conc. of std. PO}_4 \text{ solution} - \text{Conc of unbound PO}_4] \text{ mg/l}}{\text{Time (mins)}}$$

Initially when the availability of phosphate ions is high, suspensions as exemplified herein exhibit rate of phosphate binding of about 35 mg/l/min. In contrast crushed lanthanum carbonate tablets exhibit a delayed rate of phosphate binding of about 5 mg/ml/min.

The invention claimed is:

1. A liquid oral pharmaceutical composition comprising:
   (i) about 2% to about 35% lanthanum or its pharmaceutically acceptable salts thereof;
   (ii) about 0.025% to about 20% suspending agent; and
   (iii) about 60% to about 98% suspending medium that is sufficient to form a stable re suspendable suspension of said lanthanum,
   wherein the particle size diameter of the suspended particles is less than 400 μm and viscosity of suspension remains about 80 to about 97 centipoise for at least 6 months.

2. The pharmaceutical composition according to claim 1 wherein the composition comprises from about 2% to about 20% elemental lanthanum by total weight of the composition.

3. The pharmaceutical composition according to claim 1, wherein the lanthanum salt is selected from the group comprising lanthanum carbonate lanthanum hydroxy carbonate, lanthanum oxy carbonate, lanthanum oxide, lanthanum acetate, lanthanum chloride, lanthanum bromate, lanthanum iodate, lanthanum molybdate, lanthanum nitrate, lanthanum selenate, lanthanum sulfate, lanthanum tungstates, lanthanum chromate or combinations thereof.

4. The pharmaceutical composition as claimed in claim 3, wherein the lanthanum salt is lanthanum carbonate.

5. The pharmaceutical composition according to claim 4, wherein the lanthanum salt is lanthanum carbonate with 0-10 molecules of water of crystallization.

6. The pharmaceutical composition as claimed in claim 1, wherein the suspending medium is aqueous or non-aqueous.

7. A liquid pharmaceutical composition for oral administration comprising:
   (i) 2-20% of lanthanum carbonate;
   (ii) 0.025-10% of colloidal silicon dioxide;
   (iii) 0.1-15% microcrystalline cellulose;
   (iv) 0.01-5% sucralose;
   (v) 0.01-2% menthol; and
   (vi) 80-98% of suspending medium.

8. The pharmaceutical composition as claimed in claim 1, which exhibits an in-vitro release of at least 75% in 15 minutes.

9. A process for preparing a pharmaceutical composition according to claim 1, comprising the following steps:
   Step 1: measuring and transferring 70-80% of the total required quantity of suspending medium to a vessel equipped with stirring element;
   Step 2: adding a sweetening agent, flavouring agent, or antimicrobial agent to the dispersion of step 1, with continuous stirring;
   Step 3: adding lanthanum or its pharmaceutically acceptable salt and optionally a suspending agent to the mixture of step 2 and stirring for 15 to 30 min;
   Step 4: homogenizing the suspension of step 3 using suitable equipment;
   Step 5: making up the volume with suspending medium; and
   Step 6: filling the suspension of step 5 into bottles followed by secondary packing.

10. The pharmaceutical composition as claimed in claim 1, wherein the composition is used for the treatment of hyperphosphatemia.

11. A pharmaceutical composition as claimed in claim 1 wherein the composition has a sedimentation ratio of about 0.5 to about 1.

* * * * *